(12) United States Patent
Kimura et al.

(10) Patent No.: US 9,596,978 B2
(45) Date of Patent: Mar. 21, 2017

(54) MEDICAL DEVICE GUIDANCE SYSTEM

(75) Inventors: Atsushi Kimura, Akiruno (JP); Akio Uchiyama, Yokohama (JP)

(73) Assignee: OLYMPUS CORPORATION, Tokyo (JP)

( * ) Notice: Subject to any disclaimer, the term of this patent is extended or adjusted under 35 U.S.C. 154(b) by 2587 days.

(21) Appl. No.: 12/255,310

(22) Filed: Oct. 21, 2008

(65) Prior Publication Data

US 2009/0093678 A1 Apr. 9, 2009

Related U.S. Application Data

(63) Continuation of application No. PCT/JP2007/058680, filed on Apr. 20, 2007.

(30) Foreign Application Priority Data

Apr. 21, 2006 (JP) ................................. 2006-118393

(51) Int. Cl.
*A61B 5/05* (2006.01)
*A61B 1/00* (2006.01)
*A61B 1/04* (2006.01)
*A61B 5/06* (2006.01)
*A61B 5/07* (2006.01)

(52) U.S. Cl.
CPC .......... *A61B 1/00158* (2013.01); *A61B 1/041* (2013.01); *A61B 5/061* (2013.01); *A61B 5/073* (2013.01); *A61B 34/20* (2016.02); *A61B 34/70* (2016.02); *A61B 34/73* (2016.02); *A61B 90/361* (2016.02); *A61B 2034/2051* (2016.02); *A61B 2034/732* (2016.02); *A61B 2090/3954* (2016.02)

(58) Field of Classification Search
None
See application file for complete search history.

(56) References Cited

U.S. PATENT DOCUMENTS

| 2003/0016010 A1* | 1/2003 | Kandori et al. ............... 324/248 |
| 2004/0236180 A1* | 11/2004 | Uchiyama et al. ........... 600/109 |
| 2005/0062562 A1* | 3/2005 | Ries ................................. 335/1 |
| 2005/0093544 A1 | 5/2005 | Ries |
| 2005/0143642 A1* | 6/2005 | Minai et al. .................. 600/407 |

OTHER PUBLICATIONS

Extended Supplementary European Search Report dated Aug. 12, 2015 from related European Application No. 07 74 2115.4.

* cited by examiner

*Primary Examiner* — Anhtuan T Nguyen
*Assistant Examiner* — Alexandra Newton
(74) *Attorney, Agent, or Firm* — Scully, Scott, Murphy & Presser, PC

(57) ABSTRACT

The medical device guidance system include a magnetic guidance device which generates a guidance field in an arbitrary direction to guide a capsular medical device and carry out movement and posture control, a position detection device which detects the present position by a magnetic field generated by the capsular medical device and a position calculating and correcting section which forms an estimation equation of an undesired magnetic field generated from a guidance coil and subtracts an estimation equation result from the detection result of the magnetic field detecting section, according to the present position of the capsular medical device that controls the position and posture by a guidance field relative to the position detection device, and corrects the present position by excluding a desired magnetic field generated from a guidance coil.

12 Claims, 12 Drawing Sheets

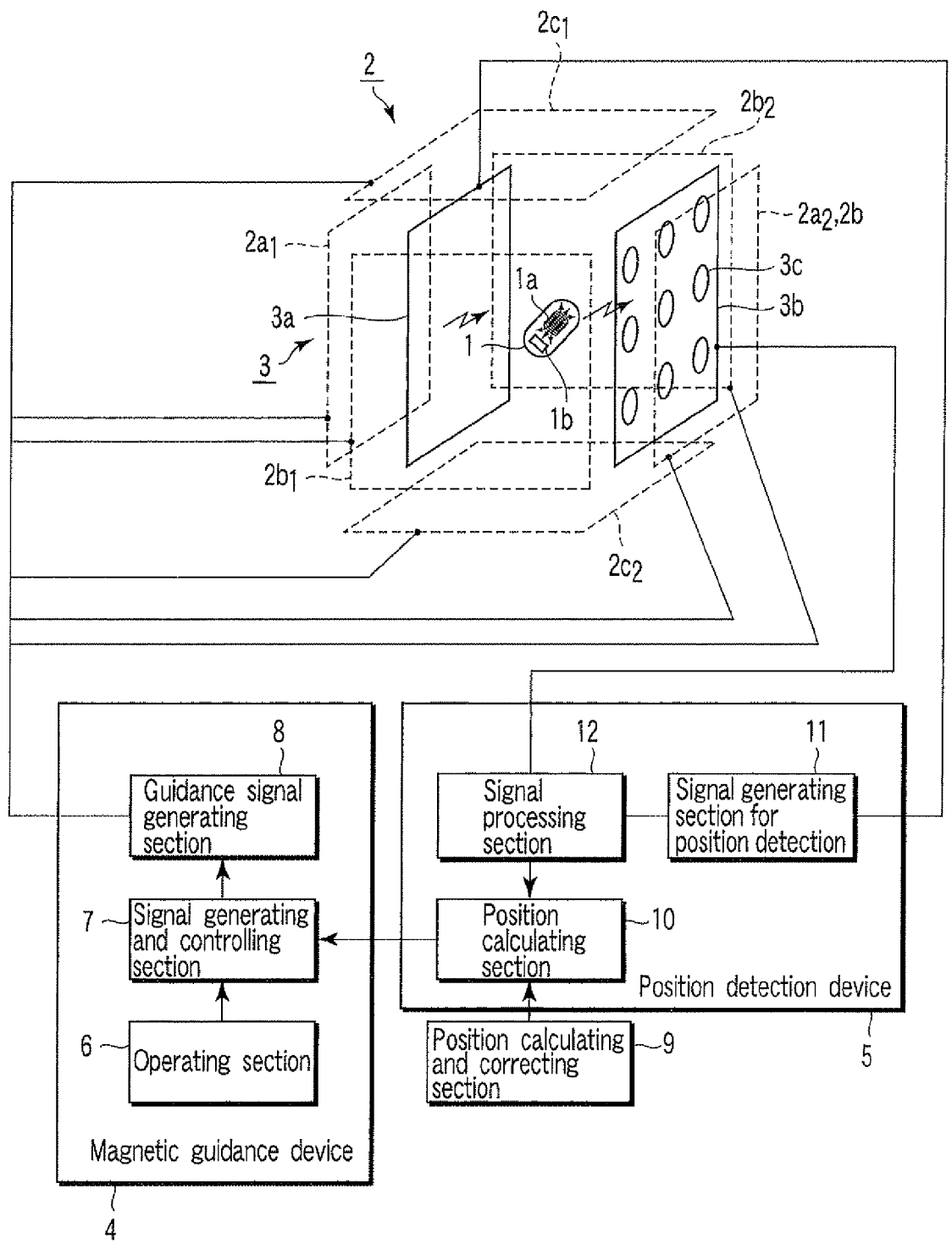
F I G. 1

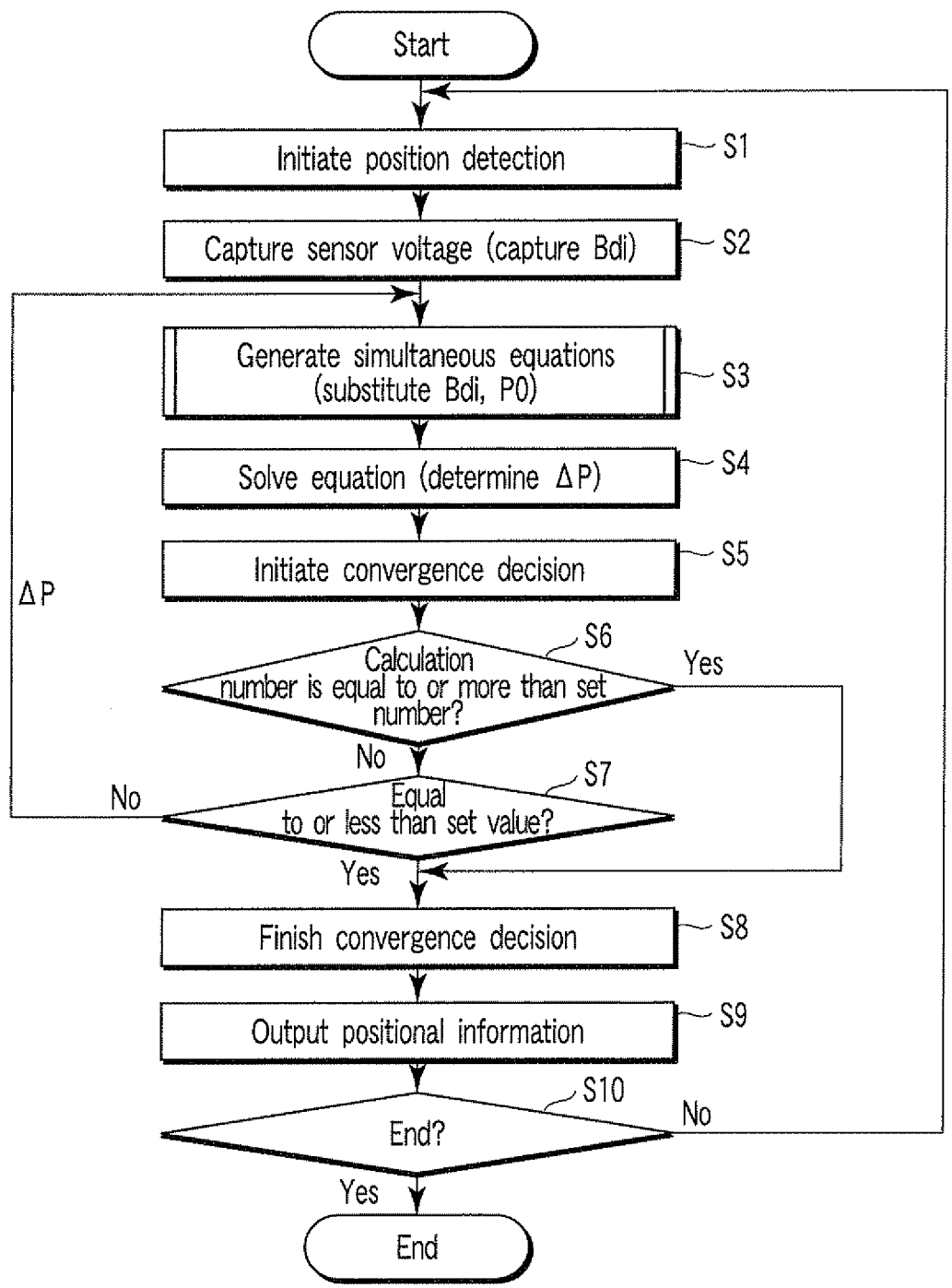
F I G. 3A

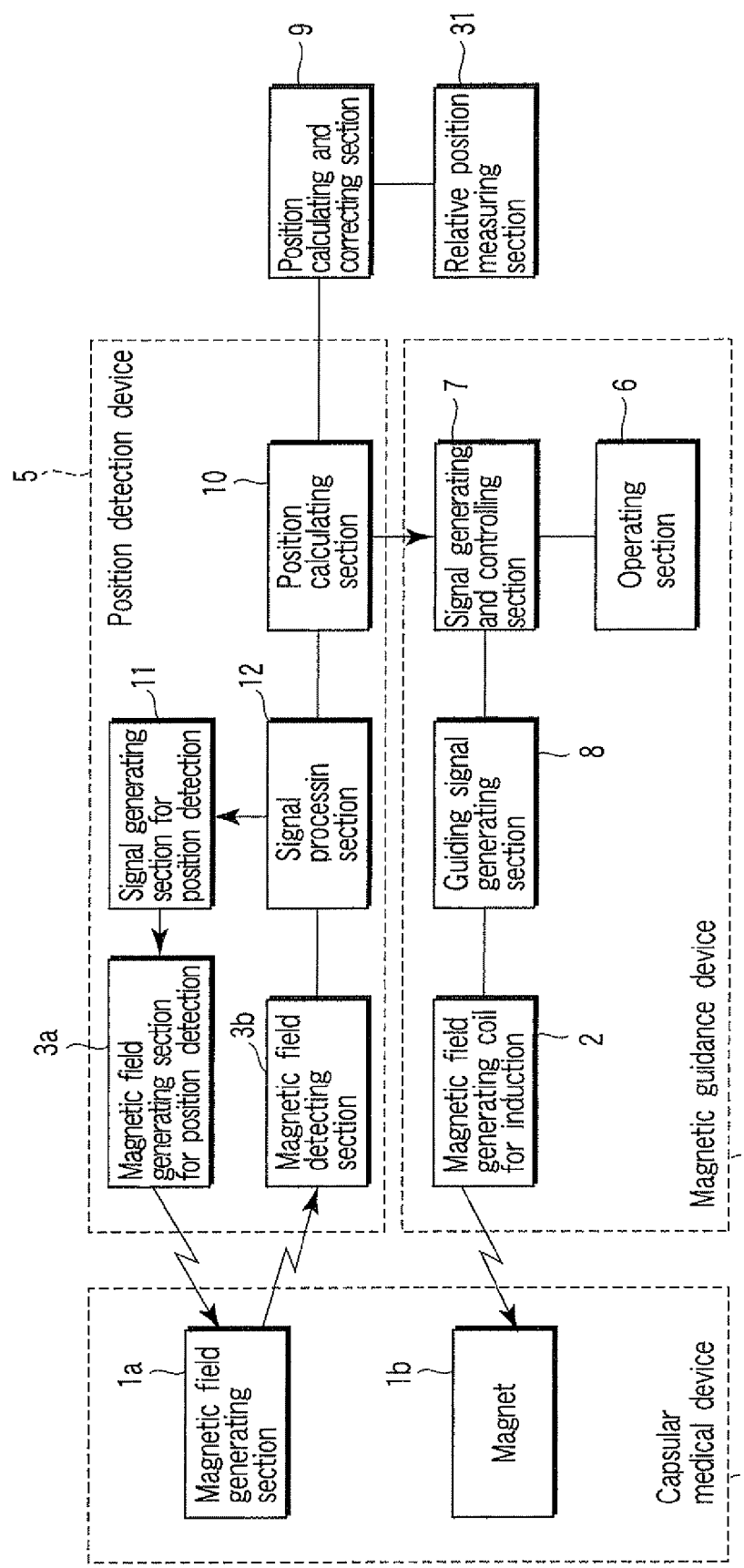
F I G. 4

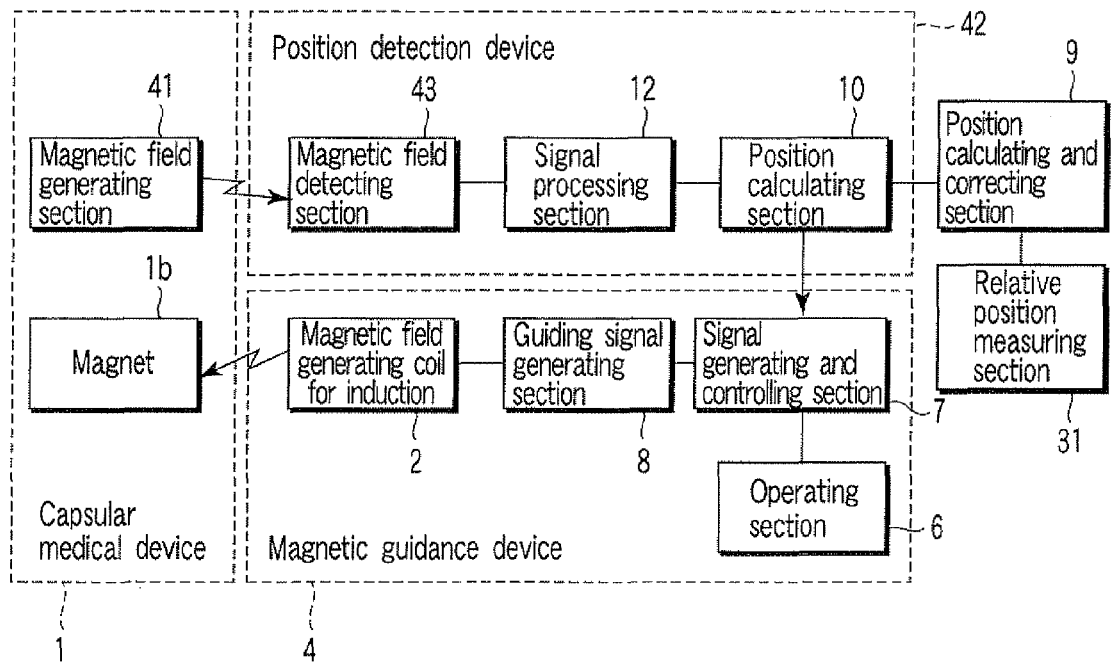
F I G. 11
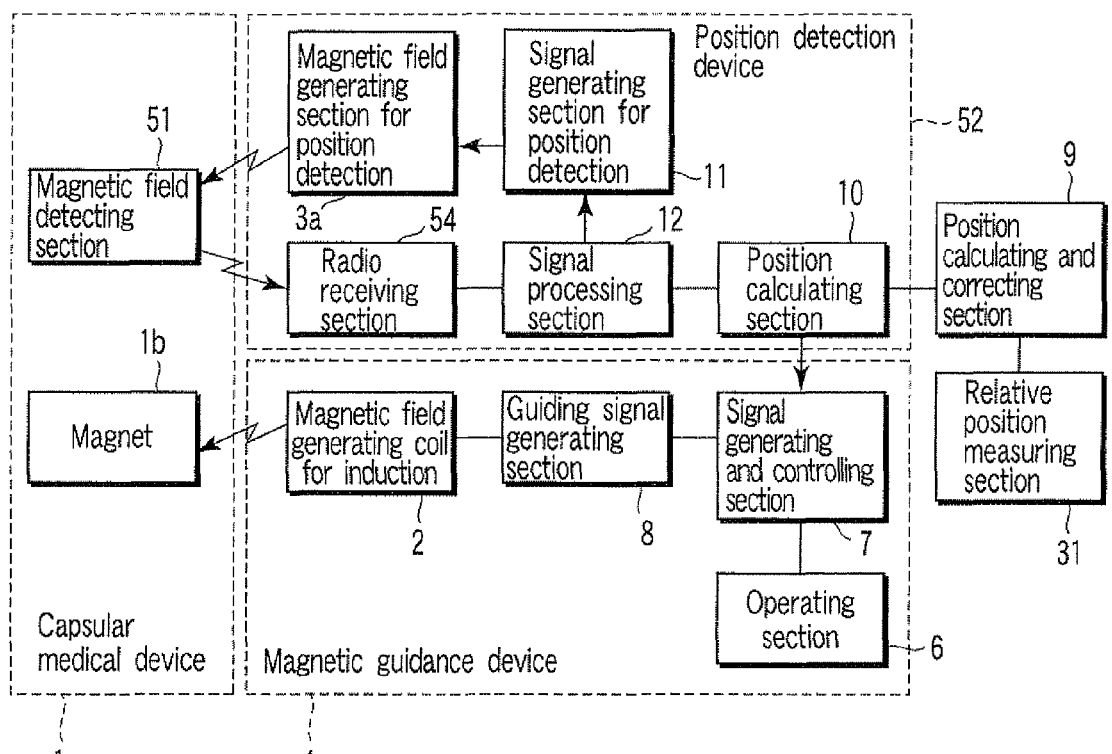
F I G. 12

MEDICAL DEVICE GUIDANCE SYSTEM

CROSS-REFERENCE TO RELATED APPLICATIONS

This is a Continuation Application of PCT Application No. PCT/JP2007/058680, filed Apr. 20, 2007, which was published under PCT Article 21(2) in Japanese.

This application is based upon and claims the benefit of priority from prior Japanese Patent Application No. 2006-118393, filed Apr. 21, 2006, the entire contents of which are incorporated herein by reference.

BACKGROUND OF THE INVENTION

1. Field of the Invention

The present invention relates to a medical device guidance system that has a position detection function of detecting the position of the medical device that passes in a gastrointestinal tract.

2. Description of the Related Art

In general, when a subject such as a patient is examined, an endoscope device that take images in the gastrointestinal tract as an image and performs monitor display is known as one medical device. Usually, an endoscope device is inserted from the oral cavity or the like and its tip has flexibility; lesions and the like to be observed are imaged by the imaging section installed on the tip side and the distal end side. A capsule endoscope is available that is different in its configuration from this capsule endoscope. The main body of this capsule endoscope, which is provided with an imaging element, is swallowed by a patient, and then passes through the gastrointestinal tract, to take image a desired target region. At this time, photograph the imaging range (angle of view) of the imaging section installed in the main body of the capsular endoscope is fixed, and thus the posture of the capsule main body needs to be controlled by guidance such that the desired target site is located within the imaging range. A system of controlling this posture involves applying a magnetic field generated from a coil installed in the surroundings, outside the body, to a magnetic field generated in the main body of a capsular endoscope, to thereby guide the main body or change the posture.

Such a guidance system is proposed, for example, in Jpn. Pat. Appln. KOKAI Publication No. 2006-026391. In this guidance system, the movement and posture are controlled by guidance field of a guidance coil arranged so as to enclose a medical device incorporating a magnet and a guidance coil by six faces. In addition, when a medical device take images a lesion or the like, its position needs to be specified. In this guidance system are disposed magnetic sensors at least in its three faces, and a position detection system, in which the position is detected by magnetic field generated from the medical device. This magnetic field sensor has arranged therein a large number of sense coils in each face for determining the position of the medical device from the magnetic intensity that each sense coil detects.

BRIEF SUMMARY OF THE INVENTION

The present invention, therefore, provides a medical device guidance system comprising: a capsular medical device including a magnet for generating a driving force by a guidance field and changing the movement and posture, and a magnetic field generating section which a coil generates a magnetic field of a specified frequency outside, the capsular medical device being introduced into a gastrointestinal tract; a magnetic guidance device including a guidance coil which radiates the guidance magnetic field, a signal generating section which flows an electric current in the guidance coil, a signal generating and controlling section which calculates a signal waveform needed for guiding the capsular medical device to a directed position and posture and an operating section which directs the movement position and posture of the capsular medical device; a position detection device including a magnetic field detecting section which has a plurality of magnetic field sensors detecting the magnetic field of the specified frequency generated by the capsular medical device and which outputs a voltage signal converted from a detected magnetic field, a signal processing section which converts the voltage signal into digital data and a position calculating section which calculates the present position of the capsular medical device from the digital data input from the signal processing section; and a position calculating and correcting section including an undesired signal equation calculating section which calculates an estimation equation of an undesired magnetic field generated in the guidance coil according to the present position of the capsular medical device and subtracts the estimation equation from the output of the magnetic field detecting section.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a diagram showing a conceptual configuration of a medical device guidance system that has a position detection function according to a first embodiment of the present invention.

FIG. 3A is a flowchart to describe position detection in the first embodiment.

FIG. 4 is a diagram showing a configuration example of a medical device guidance system that has a position detection function according to a second embodiment of the present invention.

FIG. 11 is a diagram showing a configuration example of a medical device guidance system that has a position detection function according to a seventh embodiment of the present invention.

FIG. 12 is a diagram showing a configuration example of a medical device guidance system that has a position detection function according to an eighth embodiment of the present invention.

DETAILED DESCRIPTION OF THE INVENTION

Figure 2:
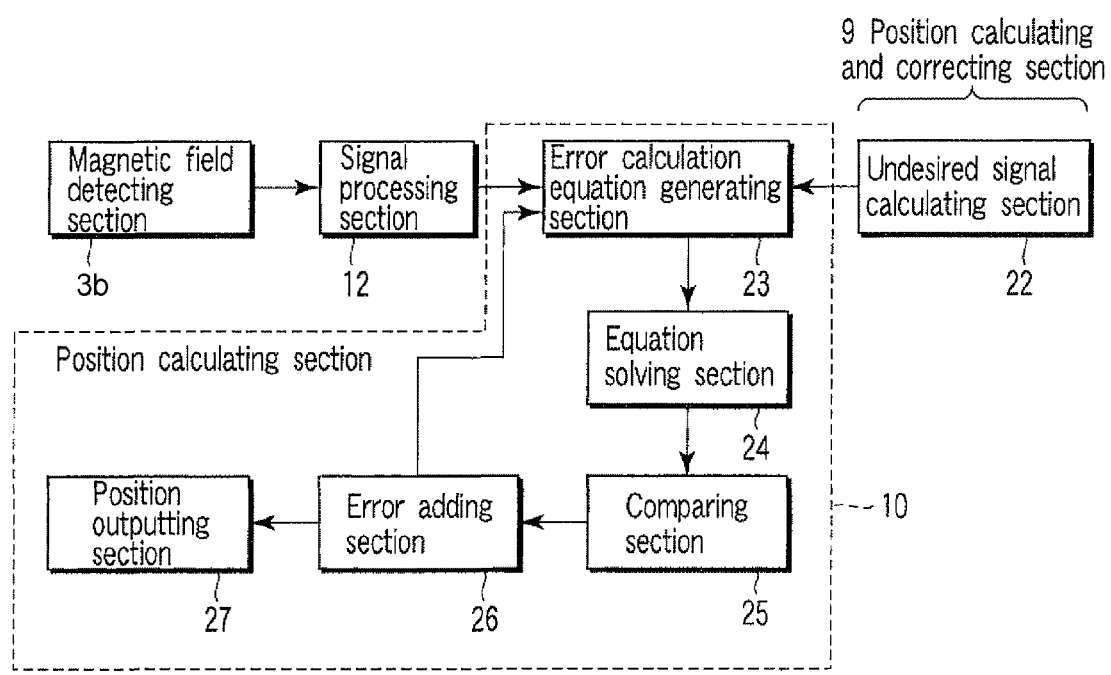
FIG. 2 is a diagram showing a position calculating section and a configuration example of a configuration site placed in its circumference in the first embodiment.

Hereinafter, embodiments of the present invention will be described with reference to the drawings. FIG. 1 is a diagram showing a conceptual configuration of a medical device guidance system that has a position detection function according to a first embodiment of the present invention.

This medical device guidance system includes, as a capsular medical device, for example, a capsular medical device 1 the position and posture of which can be controlled by a guidance field introduced into a gastrointestinal tract of a patient, a magnetic guidance device 4 for generating a magnetic field in an arbitrary direction and guiding the capsular medical device 1 to perform movement and posture control, a position detection device 5 for detecting the position by a magnetic field generated by the capsular medical device 1, and a position calculating and correcting section 9 for calculating position correction relative to the position detection device 5.

Consider, for example, the capsular medical device 1 as an example of a capsular endoscope. This capsular endoscope 1 includes an imaging section (not shown) for photographing an inner wall side of the gastrointestinal tract of a patient in a capsule container of a cylindrical geometry sealed by a watertight structure, a magnetic field generating section 1a for generating a guidance field to carry out position detection, a magnet 1b fixed to a capsular endoscope 1 and made of a permanent magnet or the like to generate a driving force for the movement and the postural change by the guidance field, and a transmission section (not shown) for converting information on imaging and a take imaged image data into communication data for transmission, and transmitting it from an antenna (not shown).

A magnetic field generating section 1a is roughly divided into a guidance type magnetic field generating section and a self-excited magnetic field generating section. The guidance type magnetic field generating section is at least composed of a resonance circuit from a guidance coil and a capacitor (parasitic capacitance or addition capacity) and resonates by action of a magnetic field for position detection to generate a magnetic field outside. In addition, a self-excited magnetic field generating section described below is composed of an oscillation circuit including a coil and generates a magnetic field of a specified frequency outside.

The magnet 1b is fixed to the rear side or to the inner circumference of the imaging section of the capsular medical device 1, and generates a force by a guidance field generated by a generation coil for a guidance field to thereby perform the movement and the postural change of the capsular endoscope 1.

A magnetic guidance device 4 is disposed in six faces so as to cover the surroundings of the capsular endoscope 1 and includes a guidance field generating coil (guidance coil: 2a1, 2a2, 2b1, 2b2, 2c1, and 2c2) 2 for generating a guidance field in an arbitrary direction, an operating section 6 that directs the moving direction and the posture that an operator intends, a signal generating and controlling section 7 that calculates a signal waveform necessary to guide the capsular endoscope 1 and controls a guidance signal generating section 8, and the guidance signal generating section 8 that flows a driving current to each of the guidance coils 2 according to the signal generating and controlling section 7 to thereby generate a guidance field.

The operating section 6 includes an input device such as a joy stick for directing the movement direction and the posture of the capsular endoscope 1 that an operator intends and a keyboard or a panel switch for executing information input and settings, and the like. The signal generating and controlling section 7 calculates a signal waveform necessary to guide the capsular endoscope 1 on the basis of the instruction of the operating section 6 and position information from a position detection device 5 and controls the guidance signal generating section 8 to generate a waveform by the result of the calculation. Hereinafter, the guidance magnetic field generating coil is called a guidance coil. In this embodiment, six guidance coils (2a1, 2a2, 2b1, 2b2, 2c1, 2c2) 2 are disposed so as to cover six faces of the surroundings of the capsular endoscope 1 (top, bottom, right, left, front and rear). The guidance coils are not limited to six coils, and may be disposed as appropriate in a suitable number according to the design.

The position detection device 5 includes a magnetic field generating section 3a for position detection, comprising a coil that generates a magnetic field to detect the position of the capsular endoscope 1, a magnetic field detecting section 3b in which a large number of magnetic field sensors 3c are arranged and which detects a magnetic field and converts it into a voltage, a signal generating section 11 for position detection that flows a driving current in a coil of the magnetic field generating section 3a for position detection to generate a position detection magnetic field of the capsular endoscope 1, a signal processing section 12 that converts a voltage signal captured by the magnetic field detecting section 3b into digital data that is necessary for positional calculation, and a position calculating section 10 that determines a digital signal input from the signal processing section to calculate positional information indicating the present position of the capsular endoscope 1 from its positional distribution data.

This signal processing section 12 further has functions of band limitation, signal amplification and analog-to-digital conversion. The magnetic field generating section 3a is arranged in the vicinity of the guidance coil of one face and generates a magnetic field for detecting the position of the capsular endoscope 1 based on the instruction of the signal processing section 12. The magnetic field detecting section 3b pinches the capsular endoscope 1, is disposed across the capsule from the magnetic field generating section 3a and has arranged therein a plurality of magnetic field sensors 3c.

The position detection in this embodiment is refers to calculation of the strength of the magnetic field output from the capsular endoscope 1 that passes through the guidance coil 2. From this value, the electromotive force to be generated in the guidance coil 2 will be calculated. The guidance coil 2 is connected to guidance signal generating section 8 with a low impedance, so that this electromotive force causes an electric current inversely proportion to the impedance of the guidance coil 2 to flow in the coil to thereby generate an undesired magnetic field.

Figure 14:
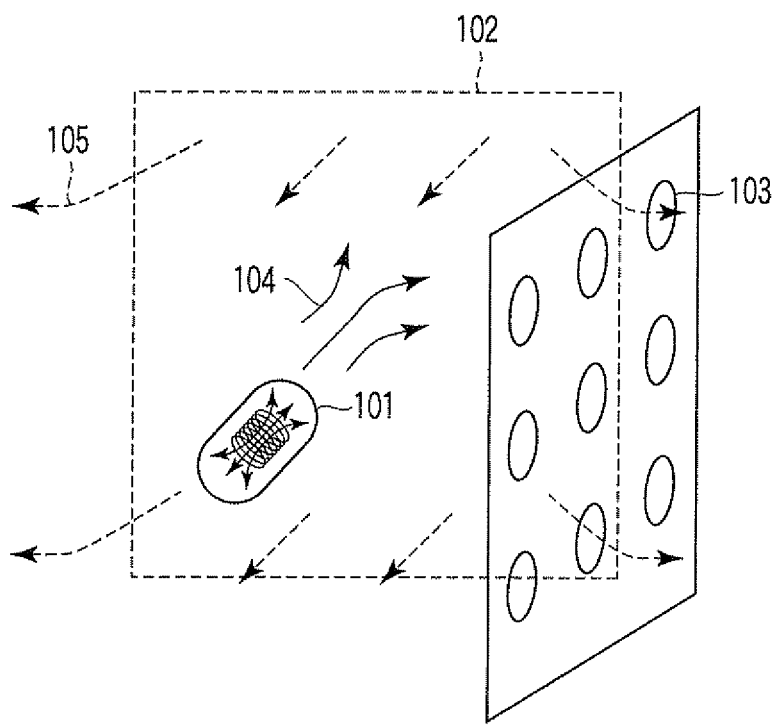
FIG. 14 is a diagram to describe an undesired magnetic field generated in a guidance coil.

A signal generation section connected to the guidance coil is characterized by having low output impedance, such that the power loss decreases when driving. Hence, an induced voltage generated by the passage of the magnetic field allows a closed circuit consisting of a guidance coil and a signal generation section to flow an electric current and to generate, unintentionally, an undesired magnetic field 105 from a guidance coil 102, as shown in FIG. 14.

Thus, a magnetic field sensor 103 will detect the total magnetic intensity, i.e., the combination of a magnetic field 104 generated by a medical device 101 and the undesired magnetic field 105. A detection value calculated from a position detecting and calculating section on the basis of this magnetic intensity gives adverse effects such as a false detection, as well as making calculation convergence impossible.

If the positional relationship between the guidance coil 2 and the magnetic field sensor 3c is clarified, the amount of electromotive force generated in each magnetic sensor 3c by the undesired magnetic field can be calculated.

FIG. 2 shows the position calculating section 10 and a configuration site placed in its circumference; the position detection will be described.

This position calculating section 10 includes an error calculation equation generating section 23, an equation solving section 24, a comparing section 25, an error addition section 26, and a position output section 27. The error calculation equation generating section 23 generates an evaluation function on the basis of positional information and posture information of an initial value (estimated position information) and the magnetic field sensor 3c, transforms the evaluation function, generates a matrix that indicates simultaneous equations the number of which is equal to the number of variables and outputs the results. In addition, the error calculation equation generating section includes a program for generating a matrix that transforms the evaluation function and expresses a simultaneous equation.

The equation solving section 24 solves an input equation and outputs its solution (error to the true value) to the comparing section 25.

The comparing section 25 compares the solution obtained by the equation solving section 24 with a threshold value (allowable error whether or not the calculation result can have been converged) and decides whether or not the calculation is continued. If the solution (error) exceeds the threshold value in this comparison processing, the error addition section 26 adds a solution of the equation to be input through the comparing section 25 to a value output from the error calculation equation generating section 23. The added result is sent to the error calculation equation generating section 23 for subsequent position calculation.

At the starting point of calculation, an initial value internally kept or input is applied. On the other hand, if the solution is smaller than the threshold value by the comparison processing, the calculation is considered to be converged and stopped; the calculation is ended and the result is output to the position output section 27.

When the number of outputs from the equation solving section 24 is counted and exceeds an arbitrary predetermined number provided in advance, the output to the error addition section is discontinued and the calculation is terminated. Such processing makes it possible to prevent more than the necessary time being consumed in a situation in which the calculation result cannot be converged. The position output section 27 receives positional information from the error addition section 26 and keeps it. In addition, when the value is converged by repeated calculation within a predetermined number of calculations, an input value to the equation solving section 24 that is kept by the error addition section 26 is acquired as positional information. On the other hand, when the value is not converged even after a predetermined number of calculations, a value that indicates no conversion (information in which the position is uncertain) is input. This positional information is output as positional information to the signal generating and controlling section 7 of the magnetic guidance device 4.

Additionally, in this configuration example, the position calculating and correcting section 9 is set to be the undesired signal calculating section 22. This undesired signal calculating section 22 is connected to the error calculation equation generating section 23 and subtracts an undesired magnetic field generated from the guidance coil 2 according to the present position of the capsular endoscope 1. Although in the evaluation function an estimated voltage calculated as a magnetic field that is produced by a magnetic dipor moment is subtracted from a measurement, an undesired signal further generated by an undesired magnetic field from this estimated voltage can be made to be calculated and subtracted.

A simultaneous equation for calculating an error from a certain estimated value is set up for an evaluation function thus obtained. In this configuration, since the position is always calculated in consideration of an undesired magnetic field, a reliable position can be estimated at any time.

Figure 3B:
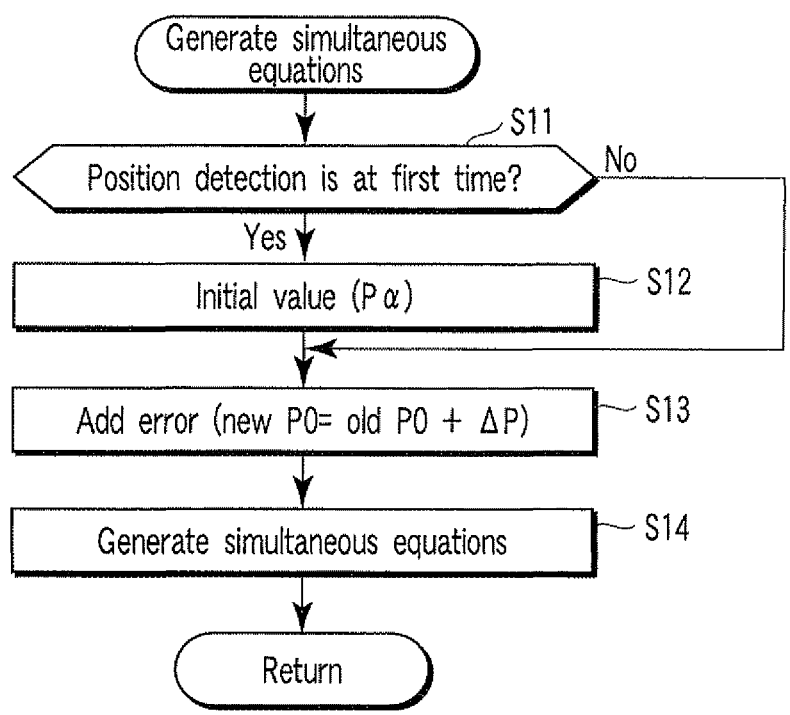
FIG. 3B is a sub-routine to describe the generation of a simultaneous equation.

FIG. 3A is a flowchart for describing position detection. FIG. 3B is a sub-routine to describe the generation of a simultaneous equation.

First, the position detection is initiated (step S1). A sensor voltage (Bdi) detected by the magnetic field sensor Sc is captured (step S2). Next, the error calculation equation generating section 23 receives an initial value (estimated position information) and the positional information of the magnetic field sensor 3c transforms an evaluation function, provided in advance, to generate a matrix that indicates simultaneous equations (step S3). Here, a sub-routine of the generation of a simultaneous equation will be described.

First, whether or not a sensor voltage (Bdi) from the magnetic field sensor 3c is a first capture and thus a first detection is decided (step S11).

If the capture is the first detection by this decision, YES is input; an initial value $P_\alpha$ set in advance is input (step S12); an error determined as described below is added to this initial value (step S13). The sensor voltage becomes an initial value $P_\alpha + \Delta P(n+1)$ after the first time. n is set to be the capture frequency on or after the second time. On the other hand, if the sensor voltage is not the first capture (No), the error is further added to the result determined last time (initial value+error). Simultaneous equations (matrix) based on a value to which an error is added are generated and output.

Next, in the equation solving section 24, the input simultaneous equations are solved and their solutions $\Delta P$ (error to the true value) are determined (step S4).

Next, the decision as to whether or not the solution obtained last time converges is initiated (step S5). This convergence decision is based on whether or not the number of calculations so far is equal to or more than the number of calculations arbitrarily set in advance (step S6). This decision is a decision for discontinuing the calculation where the solution does not converge even if the number of calculations exceeds the number of calculations defined in advance, in order to prevent the program from continuing to operate for a long time period when the calculated result cannot be converged.

If the number of calculations still does not reach the set number of calculations on the basis of this calculation (No), the solution is compared with a threshold value decision provided by the comparing section 25 (step S7). In this comparison, if the solution is smaller than the threshold value (Yes), the solution is considered to be converged and the calculation is terminated and then the convergence decision is completed (step S8). On the other hand, if the solution still exceeds the threshold value, the processing is returned to step S3 and the solution is added to the abovementioned initial value in the error addition section 26 and then output to the equation solving section 24. In this manner, the calculation is repeated until the solution determined from the equation is equal to the threshold value or less.

Then, if the convergence decision is ended, the positional information of the capsular endoscope 1 is output and whether or not the calculation is completed is decided (step S10); if the calculation is ended (Yes), the processing is returned. If the calculation is not ended yet, the processing is returned to step S1, and the position detection is made again.

Here, the position detection by magnetism will be described.

Two methods are considered to be available for the position detection by magnetism. First, when the capsular endoscope 1, which has a function of generating a magnetic field in a position detection region, is placed in a position detection region, a magnetic field generated by the capsular endoscope 1 is detected by a magnetic field sensor placed in at the periphery of the capsular endoscope 1. Second, a magnetic field sensor is embedded in the capsular endoscope 1 and detects its generated magnetic field to determine the position, when a magnetic field generation device is disposed in the surroundings. In the present invention, either of these two methods for detection is adopted.

First, the position detection for the capsular endoscope 1 that has a function of generating a magnetic field will be described as a detection target.

Firstly, a situation in which a coil is placed in a position detection region is assumed. The detection target of position detection is, for example, the capsular endoscope 1, and a situation is considered in which the capsular endoscope 1 has disposed therein a magnetic substance such as a magnet and its position and posture are controlled by an external magnetic field.

The means of magnetic field generation may be Coil, driven by an internal oscillator, or by providing a magnetic field from the outside and generating a magnetic field the guidance thereof.

When a plurality of coils is disposed in an arbitrary position as a magnetic field sensor, a voltage proportional to a magnetic flux that is present is obtained. From voltage information, a magnetic flux Bdi that passes through the i-th coil of n coils is obtained (wherein d: detected).

Assuming that a magnetic field from the capsular endoscope 1 can be regarded as a generation magnetic field from a magnetic dipole, a magnetic field at an arbitrary position can be calculated.

When the magnetic dipole moment is vector M [Mx My Mz], its position coordinate is [x, y, z] and the position vector of a place where the magnetic field is required to be determined is vector $r_{si}$ [xi, yi, zi], the position vector is expressed by vector $r_i$ [xi−x, yi−y, zi−z] and the magnetic field strength is expressed by vector B (vector $r_i$, vector M). (s: sensor position)

$$\vec{B}_i = \frac{1}{4\pi}\left\{\frac{3(\vec{M}\cdot\vec{r}_i)}{r_i^5}\vec{r}_i - \frac{\vec{M}}{r_i^3}\right\}$$

Here, the optimizing calculation of minimizing the evaluation function $$\sum_{i=1}^{n}\left(\vec{B}_{di} - \vec{B}_i(\vec{p})\right)^2$$

can be used. Vector P=(x, y, z, $M_x$, $M_y$, $M_z$) is a vector consisting of the parameter of a marker. Since the evaluation functions of the number of coils are obtained, this calculation enables vector P to be estimated.

At this time, when a coil for magnetic guidance is placed, a magnetic flux generated from the capsular endoscope 1 can pass through this guidance coil. Although this passage magnetic flux generates an induced voltage in the guidance coil, the coil is usually connected to an amplifier with a low impedance, whereby an electric current decided based on the impedance of the guidance coil actually flows, to thereby generate a magnetic field in a phase in which the electric current cancels the magnetic flux that passes through the guidance coil.

The magnetic field sensor detects the one to which a magnetic field from the guidance coil of the capsular endoscope 1 is added. Because of this, when the position is usually calculated, the result differs from a magnetic field distribution to be expected, so there may be a situation in which the correct position cannot be detected or the position calculation is not converged. However, if the configuration of the coil is decided, a magnetic field from the guidance coil can also be calculated.

In other words, if the position and the direction of the guidance coil are determined, the magnetic flux densities vector Bg(vector p) can be calculated relative to the point with the aperture of the guidance coil. (wherein, g: guidance).

Since this calculation is used to obtain an induced voltage generated in a guidance coil, a plurality of calculation points (as many as possible) is taken to thereby determine the average value $$\vec{B}_{g\_mean}(\vec{p}) = \frac{1}{N}\sum_{k=1}^{N}\vec{B}_{gk}(\vec{p})$$

The electromotive force $$\vec{B}_{g\_mean}(\vec{p})$$

is proportional to the number of turns in the guidance coils, the area and the angular frequency for Bg-mean (P), and this electromotive force is divided by the impedance to obtain the electric current which flows. In other words, the electric current $I_c$ is also a function $I_c$(vector p) of vector p. (c: cancel)

The magnetic field generated from this guidance coil is not similar to a dipole moment usually due to the coil being large; the coil is divided into a plurality of electric current vectors to which the Biot-Savart law is applied and the values of the divided number are added to be able to determine the magnetic field generated.

If the position vector of the coordinate determined when the position vector of the current element is set to be vector $r_c$ and the electric current vector is set to be vector $d_c$ is set to be vector $r_{si}$ (position of the magnetic sensor), the magnetic flux density is in calculated according to the following.

$$\vec{B}_{ci}(\vec{p}) = \oint \mu_0 \frac{I(\vec{p}) d\vec{c} \times (\vec{r}_{si} - \vec{r}_c)}{4\pi |\vec{r}_{si} - \vec{r}_c|^3}$$

The magnetic field detected by each magnetic sensor, if the position of the magnetic field relative to the guidance coil is determined, is determined in its shape of distribution. $I_C$ is set at 1 and the equation is calculated in advance and the result is held, making the situation easy. The magnetic field captured by the magnetic field sensor cancels the magnetic field B(p) generated by the capsular endoscope 1, thus the result is the sum of the magnetic fields Bc(p).

Therefore, the evaluation function in positional calculation can be set in the following.

$$\sum_{i=1}^{n} \left( \vec{B}_{di} - \vec{B}_i(\vec{p}) - \vec{B}_{ci}(\vec{p}) \right)^2$$

For this reason, even where a coil such as a guidance coil is placed, correct position detection is possible. Other coils include a coil that generates a magnetic field for position detection used in a position detection method having this induction equation magnetic field generating section. The method of an undesired magnetic field calculation is similar to the one that has been described so far.

In addition, other modification examples are present that omit the complexity of the above-described calculation. First, calculation is executed as described above to determine the position of the capsular endoscope 1. Because Bc has already been obtained, as long as the capsular endoscope 1 does not significantly move before the next detection timing, a highly accurate position can be determined more easily by subtracting it from a Bs newly detected. However, if such processing is kept, there is a fear that a problem might occur in which a deviation from the actual position occurs and the solution does not converge or the detection position suddenly moves to a different position, or the like. Because of this, a threshold value for the case of no convergence and movement distance is set. If a solution to be calculating exceeds the threshold value, an arbitrary number of applications is determined in advance and conditions when the number of applications is exceeded are set and then the error function may be used for the initial value calculation.

Second, when the capsular endoscope 1 has embedded therein a magnetic field sensor and a magnetic field generation device is disposed in the surroundings, a technique will be set forth that determines the position by detecting the generated magnetic field by the magnetic field sensor.

A magnetic field distribution to be generated or the number of magnetic field sensors for detection needs to be appropriately set in order to determine six variables of the position in the X, Y, and Z space of the capsular endoscope 1 and X, Y, Z components of the vector indicating the posture (direction) of the capsular endoscope 1.

To simplify the description, an example consisting of one magnetic field generation means and six magnetic field sensors can be understood to be the same as the method that been described so far. The six sensors are different in their disposition directions and positions. If the detection magnetic flux density is set to be Bdi, this Bdi is determined depending on the position and the posture of the capsular endoscope 1. Therefore, similarly, it is understood to only solve a problem that makes the evaluation function listed below minimum.

$$\sum_{i=1}^{n} \left( \vec{B}_{di} - B_i(p) \right)^2$$

In this case, the p vector is constituted by six components of the position x, y, z of the capsular endoscope 1 and its direction (xm, ym, zm).

Here, as described so far, an example in which a target coil for magnetic guidance or the like is placed will be considered.

If a magnetic flux from a magnetic field generation device passes through this guidance coil, the output impedance of a driver for driving the guidance coil causes an induction current to flow, generating a cancellation magnetic field.

Generation of this cancellation magnetic field causes the magnetic field sensor to detect a magnetic field different from expectation, whereby the sensor is expected to make a mistake in the detection position.

Here, if the position of the guidance coil is already known, the induction current generated by a magnetic field from a magnetic generation device is computable. Moreover, a magnetic field that a guidance coil makes at a marker position can also be calculated. This cancellation magnetic field is a function of p as indicated below.

$$\vec{B}_{ci}(\vec{p})$$

Therefore, the previous error function is also made to be embodies the equation below as described above, thereby being capable of determining p.

$$\sum_{i=1}^{n} \left( \vec{B}_{di} - \vec{B}_i(\vec{p}) - \vec{B}_{ci}(\vec{p}) \right)^2$$

This method renders it possible to detect the correct position even if the guidance coils surround with the capsular endoscope 1. In addition, even in this second example, as in the above-described other modified example, a technique for reducing the complexity of calculation can also be used.

As described thus far, the medical device guidance system having a position detection function of the first embodiment can exclude an undesired signal generated at the position detection to thereby detect the correct position of a medical device that passes through the gastrointestinal tract.

Figure 5:
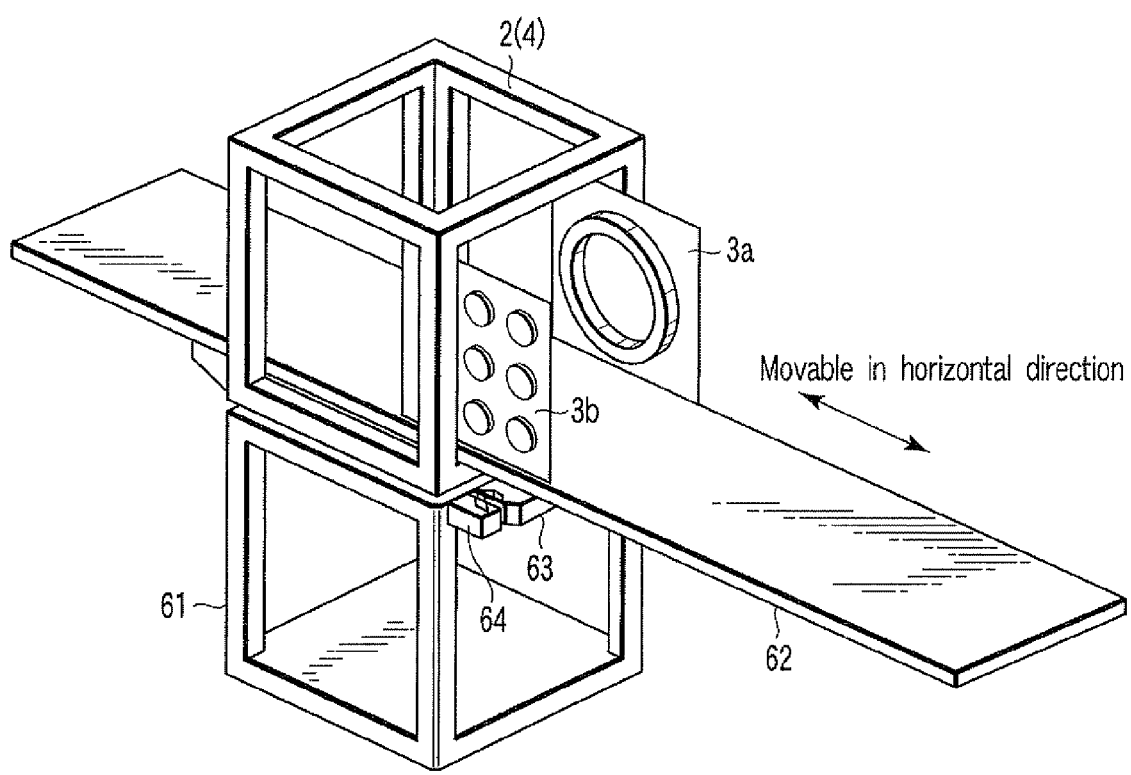
FIG. 5 is a diagram showing a configuration example of a relative position calculating section in the second embodiment.

Next, a configuration example of a medical device guidance system that has a position detection function according to a second embodiment as shown in FIG. 4 will be described. FIG. 5 shows a configuration example of a relative position measuring section 31. A configuration member of this embodiment that is equivalent to a configuration member of the first embodiment indicated in FIG. 1 depicted above will be assigned the same reference numeral and its detailed description will be omitted.

The medical device guidance system of this embodiment automatically acquires the positional information of the guidance coil and calculates an undesired signal when an undesired magnetic field is calculated, in the position calculating and correcting section 9. This medical device guidance system includes the capsular endoscope 1, the magnetic guidance device 4 that generates a guidance field, guides the capsular endoscope 1 to carry out the movement and the posture control, a position detection device 5 that detects the position of the capsular endoscope 1, the position calculating and correcting section 9 that corrects positional calculation relative to the position detection device 5, and a relative position measuring section 31 that measures the position of the guidance coil 2 relative to the reference point of the position detection device 5.

As shown in FIG. 5, the guidance coil 2 in the medical device guidance system is disposed in a frame 61. A bed 62 on which an observation object such as a patient is movably disposed in this frame in a horizontal direction. The bed 62 can electrically horizontally move by a bed actuator 63 that has a motor. A magnetic field generating section 3a for position detection and a magnetic field detecting section 3b are disposed so as to oppose each other on opposite sides of this bed.

In this example, the relative position measuring section 31 is composed of a displacement sensor 64, disposed in the vicinity of the bed actuator 63, and detects the displacement of the bed 62 as a displacement amount.

This displacement amount can specify the positional relationship from the relative distance of the guidance coil 2 and the magnetic field detecting section 3b, and therefore this position information is input to the position calculating and correcting section 9. In addition, in addition to a displacement sensor, methods are considered that involve, for example, obtaining information from an actuator used for each movement, and setting an observation index using laser measuring.

Hence, according to this embodiment, in the case of not necessarily fixing the relative position of the guidance coil and the magnetic field detecting section 3b such as a movement of a bed having placed thereon a patient, an undesired signal can be precisely calculated by addition of a relative positional relationship of the guidance coil 2 and the magnetic field detecting section 3b by use of the relative position measuring section. Additionally, the position detection of a bed can always lead to the correct calculation without manual input by updating the position relation information to automatically measure relative position relation information.

Figure 6:
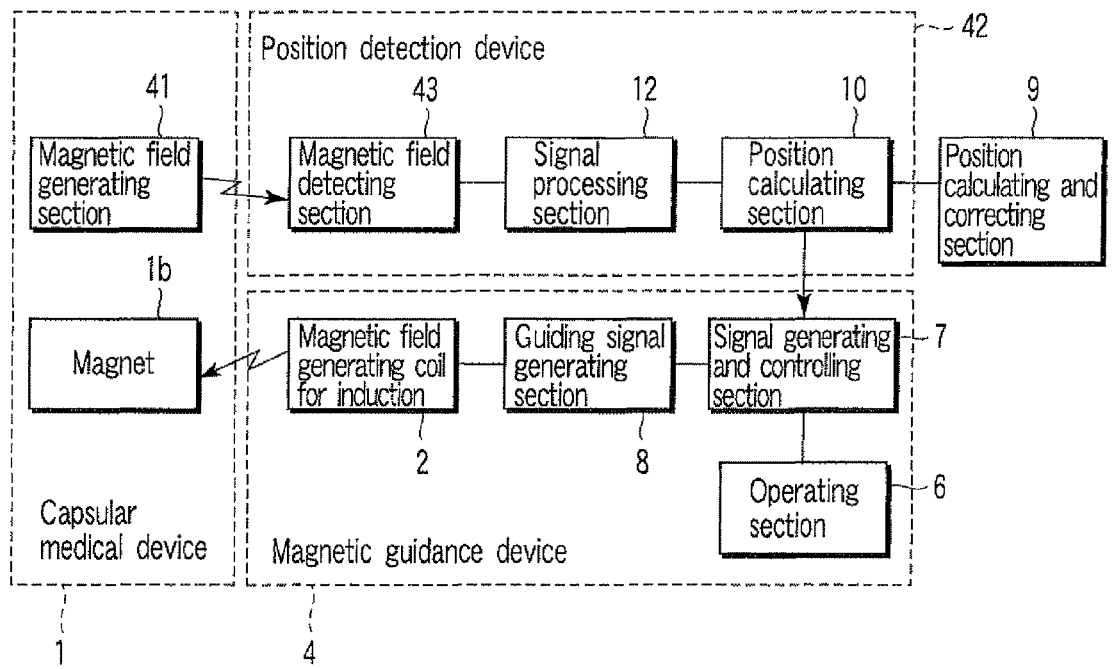
FIG. 6 is a diagram showing a configuration example of a medical device guidance system that has a position detection function according to a third embodiment of the present invention.

Next, a configuration example of a medical device guidance system that has a position detection function according to a third embodiment as shown in FIG. 6 will be described. A configuration member of this embodiment that is equivalent to a configuration member of the first embodiment indicated in FIG. 1 depicted above will be assigned the same reference numeral and its detailed description will be omitted.

This embodiment is different in the configuration of position detection from the first embodiment and includes the magnetic field generating section 41 that self-excitedly radiates a magnetic filed in place of the magnetic field generating section 1a comprising a coil within the capsular endoscope 1. The magnetic field generating section 41 includes a coil and an oscillation circuit, and powered by a battery as a power source to generate a magnetic field of a specified frequency outside.

The position detection device 42 includes a magnetic field detecting section 43 which is disposed in an arbitrary plane, has a plurality of magnetic field sensors 3c arranged in its plane and detects a magnetic field and then converts it into a voltage, the signal processing section 12 that converts a voltage signal detected by the magnetic field detecting section 43 into digital data that is necessary for positional calculation, and the position calculating section 10 that determines a digital signal input from the signal processing section to calculate positional information indicating the present position of the capsular endoscope 1 from its positional distribution data.

The present embodiment can obtain an effect equivalent to that of the first embodiment described above, exclude an undesired signal generated during the position detection and detect the correct position of a medical device that passes through the gastrointestinal tract.

Figure 7:
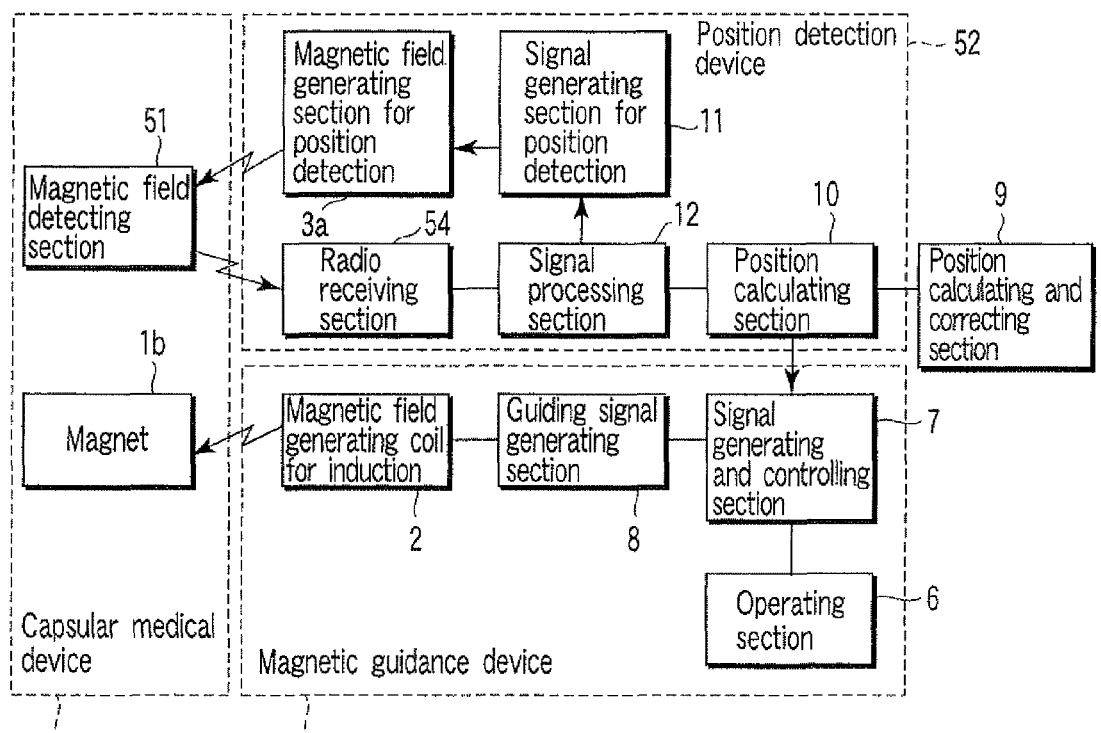
FIG. 7 is a diagram showing a configuration example of a medical device guidance system that has a position detection function according to a fourth embodiment of the present invention.

Next, a configuration example of a medical device guidance system that has a position detection function according to a fourth embodiment as shown in FIG. 7 will be described. A configuration member of this embodiment that is equivalent to a configuration member of the first embodiment indicated in FIG. 1 depicted above will be assigned the same reference numeral and its detailed description will be omitted.

The medical device guidance system of this embodiment is configured so as to have a magnetic field detecting section 51 disposed within the capsular endoscope 1, detect a magnetic field from a magnetic field generating section 53 for position detection, transmit a send data concerning the position (detection result of the magnetic field sensor) to a position detection device 52 side with a radio signal, and assess the position of the capsular endoscope 1. As described above, the magnetic field detecting section 51 within the capsular endoscope 1 detects a magnetic field generated by the magnetic field generating section 53 for position detection. In this case, interference is generated in the magnetic field generating section 53 for position detection and the guidance coil 2. As described so far, an undesired magnetic field is generated from the guidance coil 2 and added to a magnetic field for position detection, so that the distribution of a magnetic field for position detection formed in the space will change. In addition, in this configuration, the magnetic field generating section 53 for position detection is a coil as described above, whereby there is a possibility to generate an undesired magnetic field based on the same principle as the above and produce an error in position detection. In this case, an undesired magnetic field can be determined by calculation similar to the case of a guidance coil.

This medical device guidance system includes the capsular endoscope 1, the magnetic guidance device 4 that generates a guidance field, guides the capsular endoscope 1 to carry out the movement and the posture control, a position detection device 42 that detects the position of the capsular endoscope 1, and the position calculating and correcting section 9 that corrects positional calculation relative to the position detection device 42.

The capsular endoscope 1 includes at least a imaging section (not shown) within the capsule container, the magnetic field detecting section 51 that detects a magnetic field for guidance and the magnet 1b for driving the capsular endoscope 1 in a magnetic field. The magnetic field detecting section 51 detects a magnetic field for position detection generated by the magnetic field generating section 53 for position detection.

The magnetic field detecting section 51 includes a magnetic field sensor (not shown) that detects a magnetic field for position detection, a signal processing section (not shown) that converts the detected magnetic field into a voltage, generates a send data to transmitted outside the capsular endoscope 1, and a radio transmission section that sends the send data to the position detection device 42 as a radio signal. This signal processing section may be driven by installing a small battery such as a button battery within the capsular endoscope 1 or driven by an induced voltage power-generated by installing a coil for power generation and applying a magnetic field from the outside. The radio transmission section has an antenna and may also utilize an antenna for sending a take imaged image.

Figure 13:
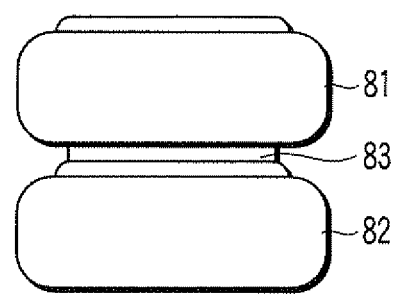
FIG. 13 is a diagram showing a joint structure of a battery provided with a capsular medical device.

In addition, when a small battery, such as button cells, are arranged in series, as shown in FIG. 13, the joint of the anode of a battery 81 and the cathode of a battery 82 may be fixed with an electroconductive double-sided tape having adhesion properties on both sides. This double-sided tape preferably has a small electric resistance and a small thickness. This configuration improves working efficiency when battery is installed within the capsular endoscope 1.

The position detection device 52 includes the signal generating section 11 for position detection that generates a position detection magnetic field from the magnetic field generating section 53 for position detection, the magnetic field generating section 53 for position detection that generates a magnetic field for position detection relative to the magnetic field detecting section 51 disposed within the capsular endoscope 1, a radio receiving section 54 that receives a radio signal (send data) indicating the location of the capsular endoscope 1 transmitted from the radio transmitting section, the signal processing section 12 that converts a voltage signal based on a radio signal received in the radio receiving section 54 into digital data necessary for positional calculation, and the position calculating section 10 that assesses a digital signal input from the signal processing section and calculates the positional information of the capsular endoscope 1 from its voltage data.

As described so far, this embodiment includes the above-described position calculating and correcting section 9 and carries out no-position calculation based on the generation of a magnetic field for position detection passed through the guidance coil 2, thus being capable of excluding adverse effects such as false detection as well as being incapable of convergent calculation.

Figure 8:
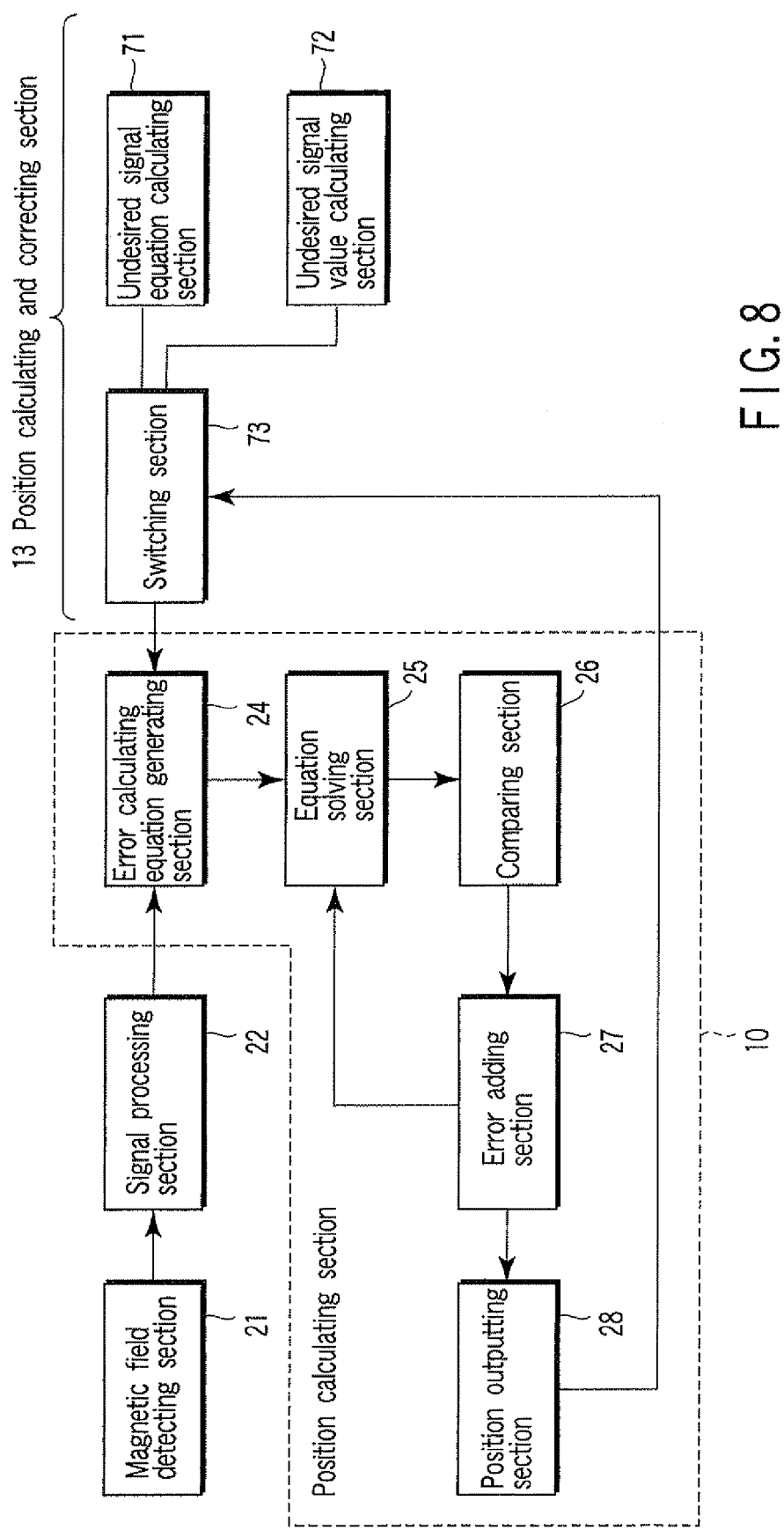
FIG. 8 is a diagram showing a configuration example of a medical device guidance system that has a position detection function according to a fifth embodiment of the present invention.

Next, a configuration example of a medical device guidance system that has a position detection function according to a fifth embodiment as shown in FIG. 8 will be described. A configuration member of this embodiment that is equivalent to a configuration member of the first embodiment indicated in FIG. 2 depicted above will be assigned the same reference numeral and its detailed description will be omitted.

In this embodiment, the position calculating section 10 includes the error calculation equation generating section 23, the equation solving section 24, the comparing section 25, the error addition section 26, and the position output section 27.

The position calculating and correcting section 13 includes an undesired signal equation calculating section 71 that calculates an estimation equation of an undesired magnetic field generated from a guidance coil according to the position of the capsular endoscope 1 and subtract the undesired magnetic field from the magnetic field generated from the guidance coil, an undesired signal value calculating section 72 that calculates an estimation equation of an undesired magnetic field value (no variables) generated from a guidance coil from detection position information and subtracts, subtract the undesired magnetic field value from an magnetic field value generated from the guidance coil, and a switching section 73 that executes two kinds of decisions according to set conditions and switching the undesired signal equation calculating section or the undesired signal value calculating section.

In an actual movement, when the distance moved of the capsular endoscope 1 in a gastrointestinal tract is small, a situation in which the interference state of the capsular endoscope 1 and the guidance coil 2 normally does not change. Meanwhile, even when the displacement is not so large, the variation of the interference might also be large when the interval between the capsular endoscope 1 and the guidance coil is small.

The medical device guidance system of this embodiment is configured so as to switch the evaluation function according to a situation. When the position is firstly calculated, the guidance coil 2 is provided as in the configuration of the first embodiment, and the correct position is detected on the basis of the calculation result to which the undesired signal equation calculating section is applied. Thereafter, the value of an undesired signal is regarded as having a small variation and used by subtracting a resulting undesired signal (no variables) from a data value measured from the position previously detected.

In addition, by comparison of a calculation result to which the undesired signal equation calculating section is applied and a positional calculation result by a simplified method based on the subsequent measurement data, when the difference exceeds a predetermined threshold value, the capsular endoscope 1 actually moves significantly, or though the movement is small, the amount of interference is large, generating an error in positional calculation. In this case, correct calculation that uses the undesired signal equation calculating section 71 is necessary. Therefore, in this embodiment, by comparison of a calculation result to which the undesired signal equation calculating section is applied and a positional calculation result by a simplified method based on the subsequent measurement data, only when the positional displacement is large, the error calculation is made in equation form to reflect it in convergent calculation.

Figure 9:
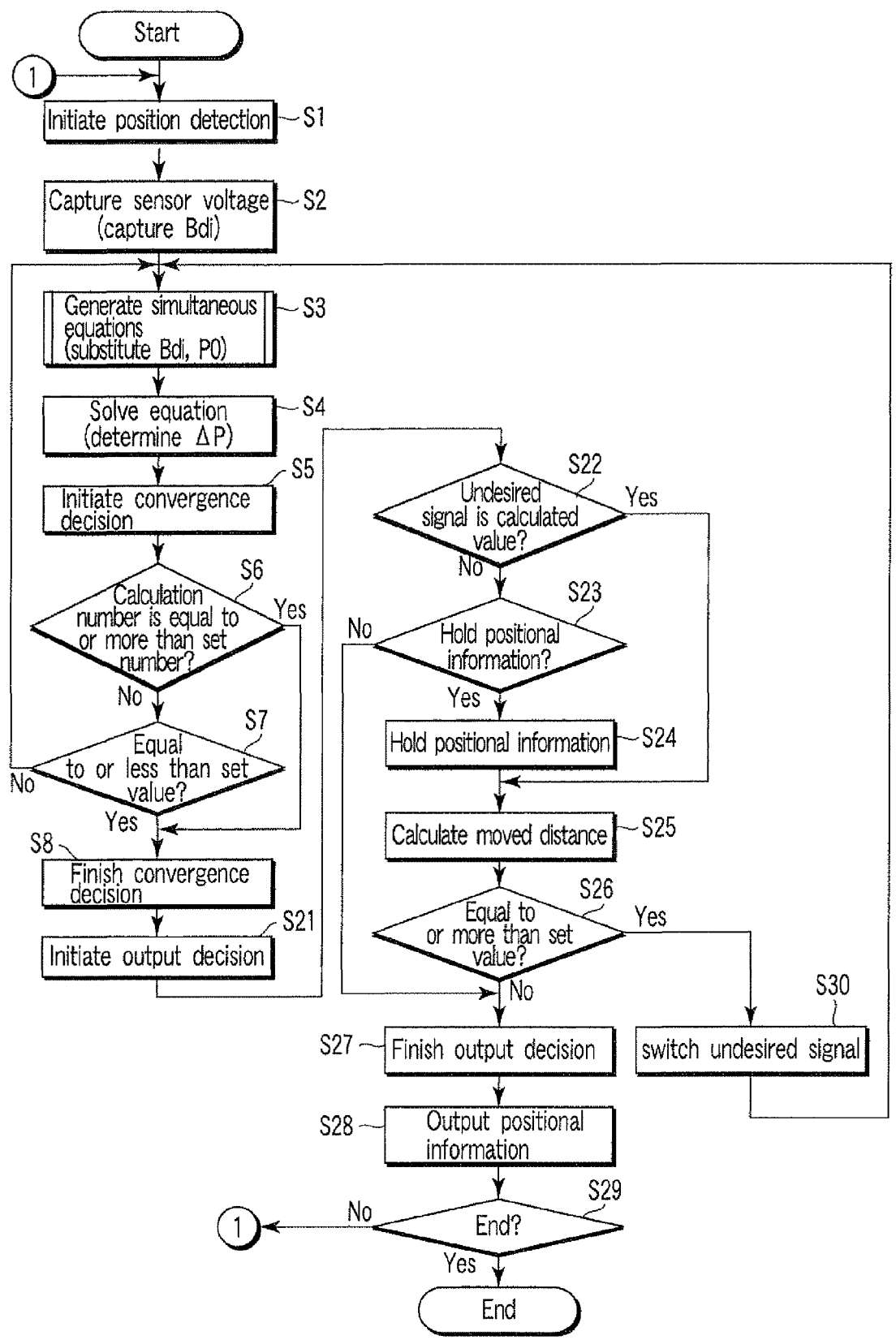
FIG. 9 is a flowchart to describe position detection of the medical device guidance system in the fifth embodiment.

Referring to a flowchart shown in FIG. 9, the position detection of a medical device guidance system configured in this manner will be set forth.

A detection operation of this embodiment that is equivalent to each detection operation of the flowchart indicated in FIGS. 3A and 3B depicted above will be assigned the same step number and its detailed description will be omitted.

First, position detection is initiated and a sensor voltage (Bdi) detected by the magnetic field sensor $3c$ is captured. Next, the error calculation equation generating section 23 receives an initial value (estimated position information) and the positional information of the magnetic field sensor $3c$, and transforms an evaluation function provided in advance to generate a matrix that indicates simultaneous equations (steps S1 to S3). Next, in the equation solving section 24, the input simultaneous equations are solved and their solutions ΔP (errors to the true values) are determined and then the decision as to whether or not the determined solutions are converged relative to the previously determined solutions is initiated. This convergence decision is based on whether or not the number of calculations so far is equal to, more than, or less than a set number of calculations. In this decision, if the number of calculations is equal to or more than a set number or if the solution is equal to smaller than a set value, the calculation is terminated and then the convergence decision process is ended (steps S4 to S8).

Next, output decision processing is initiated (step S21). First, the decision on whether or not an undesired signal used immediately before is determined by calculation is made (step S22). If the undesired signal is a calculated value by this decision (Yes), the value is decided to indicate the correct position and thus the distance moved calculation is executed (step S25).

On the other hand, if the undesired signal is not a calculated value (No), it is decided to be a positional calculation result obtained by the simplified method. Next, whether or not this positional information is held is decided (step S23). If the positional information is held by this decision (Yes), the position output section 27 receives positional information from the error addition section 26 and keeps it (step S14). On the other hand, if the positional information is not held (No), the output decision processing is ended (step S27).

Next, the distance moved from the last position is calculated on the basis of this retained positional information (step S25). Whether or not the calculated distance moved is equal to or more than an arbitrary set value in advance is decided (step S26). If the distance moved is more than the set value by this decision (Yes), it is decided that the capsular endoscope 1 is actually significantly moved, or that the amount of interference is greatly changed although the device is not moved and an error is generated by positional calculation. In other words, the evaluation function needs to be altered and an undesired signal is switched in order to determine a calculated result to which the undesired signal equation calculating section is applied (step S30). The switch of this undesired signal is a switch by positional calculation using the calculation equation or by positional calculation by the simplified method using a measured data. In addition, in the switch to positional calculation using the calculation equation, an undesired signal equation is generated only at the initial time.

Additionally, if the distance moved is less than the threshold value by the decision of step S26 (No), the distance value is converged equal to or less than the set value. The determined positional information is decided to be precise and the output decision processing is ended (step S27). Then, the positional information is output from the position output section 27 to the signal generating and controlling section 7 (step 328). Moreover, after this output, whether or not this position detection is continued is decided (step S29). If the position detection is not ended (No), the processing is returned to step S1, and the position detection is made again.

If the position detection is not continued (Yes), and a series of sequences are ended.

As described above, accurate positional information may always be determined by the equation of the undesired signal equation calculating section. However, the calculation is configured so as to switch the evaluation function according to the situation to thereby detect the correct position firstly on the basis of position calculation. Thereafter, the value of an undesired signal is regarded as having a small variation and used by subtracting a resulting undesired signal (no variables) from data value measured from the position previously detected to thereby achieve speed-up of position detection in which operation processing is simplified.

In addition, a calculation result to which the undesired signal equation calculating section is applied is compared with a positional calculation result obtained by the simplified method based on the subsequent measurement data in terms of the distance moved. When a calculation result obtained by the simplified method based on the measurement data has a large error due to the comparison of the difference (difference of the distance moved) with a predetermined threshold value, the correct positional information may be determined again by the equation of the undesired signal equation calculating section.

Therefore, the amount of calculation in the system can be substantially reduced because the undesired signal calculating section is output only when a precise calculation is executed again. As a result, this embodiment is configured so as to achieve speed-up while maintaining precise position detection by calculating the position by selective use of the calculation result.

Figure 10:
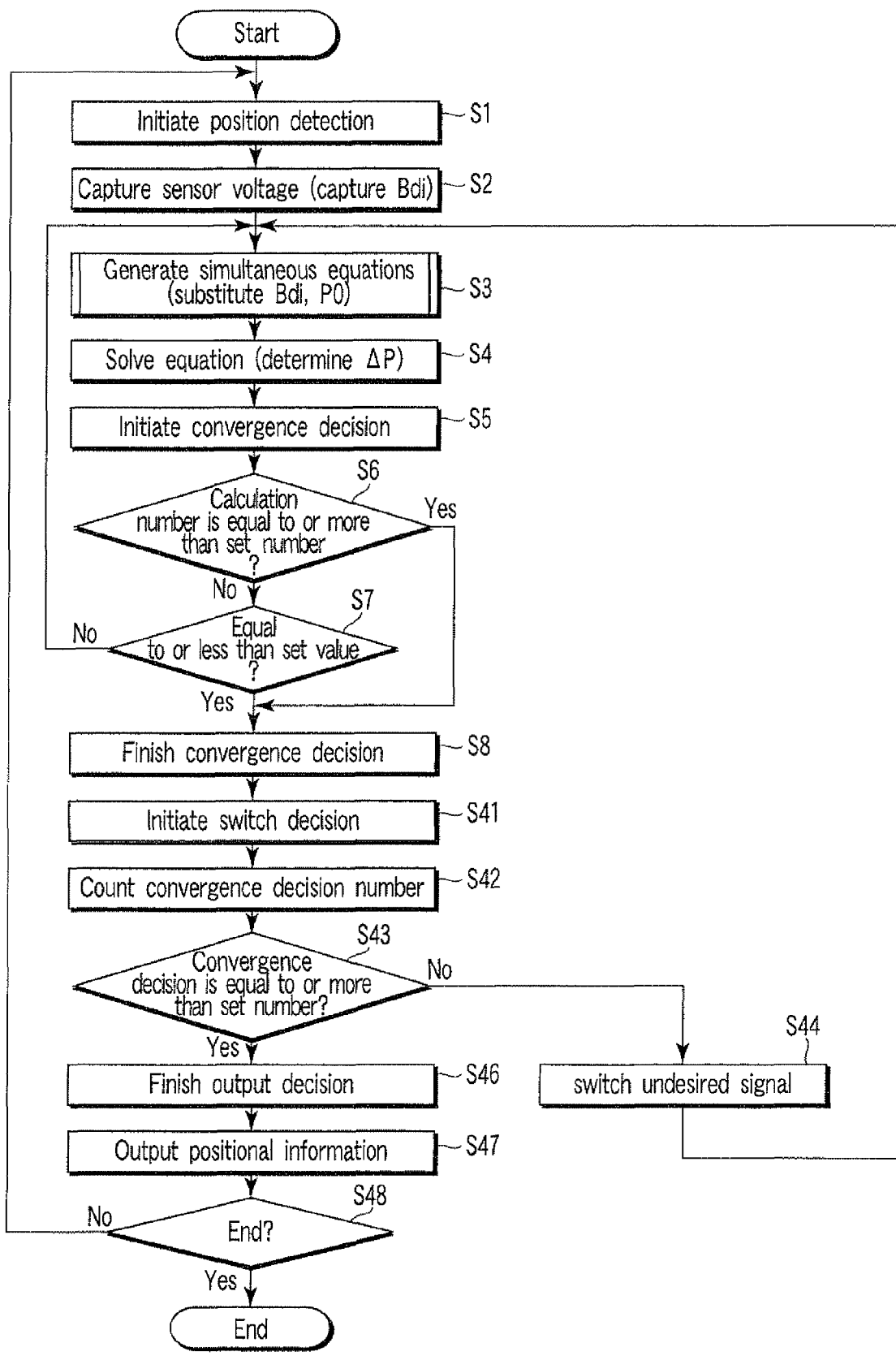
FIG. 10 is a diagram showing a configuration example of a medical device guidance system that has a position detection function according to a sixth embodiment of the present invention.

Next, a configuration example of a medical device guidance system that has a position detection function according to a sixth embodiment as shown in FIG. 10 will be described. A configuration member of this embodiment that is equivalent to a configuration member of the first embodiment indicated in FIG. 8 depicted above will be assigned the same reference numeral and its detailed description will be omitted.

In the above-described fifth embodiment, the size of the difference between the correct calculation result to which the undesired signal equation calculating section is applied and a simple calculation result (measurement data) to which the undesired signal equation calculating section is applied was decided in terms of the distance moved. On the other hand, this embodiment is an example of making the switch decision in terms of number of decisions.

A detection operation of this embodiment that is equivalent to each detection operation of the flowchart indicated in FIGS. 3A and 3B depicted above will be assigned the same step number and its detailed description will be omitted.

First, a decision evaluation function is modified to form a matrix expressing simultaneous equations and solve the simultaneous equations, and then whether or not the solutions are converged is decided (steps S1 to S8).

Next, after convergence decision processing in step S8 ends, the switch decision on the undesired signal equation calculating section 71 and the undesired signal value calculating section 72 is initiated (step S41). The number of convergence decisions made in steps S3 to S8 is counted (step S42). Whether or not this counted convergence decision number is equal to or more than the arbitrarily set number of decisions is decided (step S43). If the number of convergence decision is equal to or less than the set number by this decision (No), there is still a possibility of convergence by the modification of the evaluation function. Hence, the switch on the undesired signal equation calculating section 71 and the undesired signal value calculating section 72 is made (step S44). At this time, only at the initial switch, an undesired signal equation is generated. Moreover, at the time of the switch, the count number of the counter is set at 0.

On the other hand, if the convergence decision number is equal to or more than the set number (Yes), the output decision is made terminated (step S46). Then, the positional information is output from the position output section 27 to the signal generating and controlling section 7 (step S47). Moreover, after this output, whether or not the position detection is continued is decided (step S48). If the position detection is not ended (No), the processing is returned to step S1, and the position detection is made again. If the position detection is not continued (Yes), and a series of sequences are ended.

This embodiment compares the decision number with a set number as described above. When the decision number exceeds the initial and set number for the calculation, the equation by the undesired signal equation calculating section is applied. Excluding that, simple previous positional information provided by the undesired signal value calculating section is used and the embodiment is based on the subtraction of the calculated undesired signal (no variables). The decision for carrying out the switch decision in the above-described fifth embodiment is only changed to the number, and an equivalent effect can be obtained. In addition, this embodiment has no distance moved operation and simply has an execution number of convergence decision. Therefore, the amount of calculation can be decreased, and the switch decision can be made by a simple configuration.

Next, a configuration example of a medical device guidance system that has a position detection function according to a seventh embodiment as shown in FIG. 11 will be described. A configuration member of this embodiment that is equivalent to a configuration member of the third embodiment indicated in FIG. 6 depicted above will be assigned the same reference numeral and its detailed description will be omitted.

This embodiment is a modified example in which a relative position measuring section shown in FIG. 4 is added to a configuration example of a medical device guidance system that has a position detection function according to the third embodiment described above. Here, only changed features will be described.

This embodiment includes the relative position measuring section 31 that is a medical device guidance system corresponding to the capsular endoscope 1 which has a self-excited magnetic field generating section and that measures the position of the guidance coil 2 to the reference point of the position detection device 5.

According to this embodiment, in the case of not fixing the relative position of the guidance coil and the magnetic field detecting section 3b that detects the position, an undesired signal can be precisely calculated by addition of a relative positional relationship of the guidance coil 2 and the magnetic field detecting section 3b by use of the relative position measuring section. Additionally, the position detection of a bed can always lead to the correct calculation without manual input by updating the position relation information to automatically measure relative position relation information.

Next, a configuration example of a medical device guidance system that has a position detection function according to an eighth embodiment is shown in FIG. 12 and will be described. A configuration member of this embodiment that is equivalent to a configuration member of the third embodiment indicated in FIG. 6 depicted above will be assigned the same reference numeral and its detailed description will be omitted.

This embodiment is a modified example in which a relative position measuring section shown in FIG. 4 is added to a configuration example of a medical device guidance system that has a position detection function according to the third embodiment described above. Here, only changed features will be described.

The medical device guidance system of this embodiment includes the relative position measuring section 31 that is a medical device guidance system corresponding to the capsular endoscope 1 which has a self-excited magnetic field generating section and that measures the position of the guidance coil 2 to the reference point of the position detection device 5. This embodiment has an effect equivalent to the above-described seventh embodiment.

According to the present invention, there can be provided a medical device guidance system that excludes an undesired signal generated during position detection and has a position detection function of detecting a precise position of a medical device that passes in a gastrointestinal tract and its position correction method.

Although a guidance system for a medical device can been described in each embodiment described above, an effect of a like position detection correction can be expected also in the position detection system that has a magnetic field generating section for position detection. For instance, in the first embodiment, the guidance system for a medical device is effective even in the position detection system that removes the magnetic field generating coil 2 and the guidance signal generating section 8. In this case, because the magnetic field generating section 3a for position detection generates an undesired magnetic field, the determination of this undesired magnetic field by calculation makes it possible to precisely detect the position/direction as having been described so far.

What is claimed is:

1. A medical device guidance system comprising:
a capsular medical device including a magnet for generating a driving force by a guidance field and changing the movement and posture, and a magnetic field generating section which a coil generates a magnetic field of a specified frequency outside, the capsular medical device being introduced into a gastrointestinal tract;
a magnetic guidance device including a guidance coil which radiates the guidance magnetic field, a signal generating section which flows an electric current in the guidance coil, a signal generating and controlling section which calculates a signal waveform needed for guiding the capsular medical device to a directed position and posture and an operating section which directs the movement position and posture of the capsular medical device;
a position detection device including a magnetic field detecting section which has a plurality of magnetic field sensors detecting the magnetic field of the specified frequency generated by the capsular medical device and which outputs a voltage signal converted from a detected magnetic field, a signal processing section which converts the voltage signal into digital data and a position calculating section which calculates the present position of the capsular medical device from the digital data input from the signal processing section; and
a position calculating and correcting section including an undesired signal calculating section which calculates an estimation equation of an undesired magnetic field generated in the guidance coil due to external magnetic fields intersecting the guidance coil or the signal generating section and subtracts the estimation equation from the output of the magnetic field detecting section.

2. The medical device guidance system according to claim 1, wherein the signal processing section further comprises functions of band limitation, signal amplification and analog-to-digital conversion.

3. The medical device guidance system according to claim 1, further comprising:

a relative position measuring section which measures the position of the guidance coil relative to the reference point of the position detection device.

4. The medical device guidance system according to claim 1, wherein the position calculating and correcting section comprises:
the undesired signal equation calculating section;
an undesired signal value calculating section which subtracts an undesired magnetic field generated from the guidance coil that is estimated according to the positional information of the capsular medical device measured; and
a first switching section which compares a distance moved based on the measured positional information with an arbitrary set value set in advance and, if the distance moved is equal to or more than the set value, selects the undesired signal equation calculating section to carry out the position calculation and, if the distance moved is less than the set value, selects the undesired signal value calculating section to carry out the position calculation.

5. The medical device guidance system according to claim 1, wherein the position calculating and correcting section comprises:
the undesired signal equation calculating section;
an undesired signal value calculating section which subtracts an undesired magnetic field generated from the guidance coil that is estimated according to the positional information of the capsular medical device measured; and
a second switching section which counts a detection number in the position detection device and, when the detection number exceeds an arbitrary set number set in advance, selects the undesired signal equation calculating section to carry out the position calculation and, when the counted detection number is equal to or less than the set number, selects the undesired signal value calculating section to carry out the position calculation.

6. A medical device guidance system comprising:
a capsular medical device including a second magnetic field generating section which has a resonance circuit comprising a magnet and a guidance coil and a capacitor for generating a driving force by a guidance field and generates a magnetic field of a specified frequency outside by resonance by a magnetic field for position detection;
a magnetic guidance device including a guidance coil which radiates the guidance magnetic field, a signal generating section which flows an electric current in the guidance coil, a signal generating and controlling section which calculates a signal waveform needed for guiding the capsular medical device to a directed position and posture and an operating section which directs the movement position and posture of the capsular medical device;
a position detection device including a magnetic field detecting section which has a plurality of magnetic field sensors for detecting the magnetic field of the specified frequency generated by the capsular medical device and which outputs a voltage signal converted from the detected magnetic field, a signal processing section which converts the voltage signal into digital data, a position calculating section which calculates the present position of the capsular medical device from the digital data input from the signal processing section and a magnetic field generating section for position detection which has a signal generating section and a magnetic field generating coil for position detection and generates a magnetic field for position detection; and
a position calculating and correcting section including an undesired signal equation calculating section which calculates an estimation equation of an undesired magnetic field generated in the guidance coil and the magnetic field generating coil for position detection according to the present position of the capsular medical device and subtracts the estimation equation from the output of the magnetic field detecting section.

7. A medical device guidance system comprising:
a position detection device including a capsular medical device which is introduced into a gastrointestinal tract, is capable of movement and posture, control by the generation of driving force caused by a guidance field and always or by response generates a magnetic field of a specified frequency, a magnetic field detecting section of detecting a magnetic field of the specified frequency and a position detecting section of detecting a position in a gastrointestinal tract of the capsular medical device on the basis of the detection result of the magnetic field detecting section;
one or more coils arranged in the surrounding of the capsular medical device and making up of a closed circuit;
an undesired signal value calculating section which calculates an undesired signal on the basis of an undesired magnetic field generated by the magnetic field of the specified frequency that enters into the coil; and
a position calculating and correcting section which subtracts a calculation result by the undesired signal value calculating section from a detection result of the magnetic field detecting section to thereby exclude a magnetic field that corresponds to the undesired magnetic field.

8. The medical device guidance system according to claim 7, comprising:
a relative position measuring section which measures the position of the coil relative to the reference point of the position detection device.

9. The medical device guidance system according to claim 7, further comprising:
an undesired signal equation calculating section which calculates an estimation equation for estimating an undesired magnetic field to be generated in the coil subtracted from the output of the magnetic field detecting section according to the present position of the capsular medical device.

10. The medical device guidance system according to claim 9, further comprising:
a first switching section which compares a distance moved based on the measured positional information with an arbitrary set value set in advance and, if the distance moved is equal to or more than the set value, selects the undesired signal equation calculating section to carry out the position calculation and, if the distance moved is less than the set value, selects the undesired signal value calculating section to carry out the position calculation.

11. The medical device guidance system according to claim 9, comprising:
a second switching section which counts a detection number in the position detection device and, when the detection number exceeds an arbitrary set number set in advance, selects the undesired signal equation calculating section to carry out the position calculation and, when the counted detection number is equal to or less than the set number, selects the undesired signal value calculating section to carry out the position calculation.

12. The medical device guidance system according to claim 9, wherein the specified frequency generating section has a resonance circuit comprising a guidance coil and a capacitor, is connected to the coil, has a signal generating section which supplies the electric current of the specified frequency to the coil and receives a magnetic field that has the specified frequency to generate and induce a magnetic field of the specified frequency.

* * * * *